United States Patent
Uhoch

[11] Patent Number: 5,554,293
[45] Date of Patent: Sep. 10, 1996

[54] DISPOSABLE BLOOD WASHING AND APHERESIS DEVICE AND METHOD OF USING THEREOF

[75] Inventor: John Uhoch, Warwick, R.I.

[73] Assignee: C. R. Bard, Inc., Murray Hill, N.J.

[21] Appl. No.: 83,618

[22] Filed: Jun. 28, 1993

[51] Int. Cl.[6] .......................... B01D 61/00; B01D 65/00;
  B01D 36/00; B01D 37/00
[52] U.S. Cl. .................... 210/650; 210/85; 210/94;
  210/97; 210/136; 210/198.1; 210/252; 210/258;
  210/321.69; 210/418; 210/433.1; 210/435;
  210/651; 210/739; 210/791
[58] Field of Search ........................ 210/645, 650,
  210/651, 85, 134, 136, 252, 257.2, 258,
  929, 321.65, 117, 321.67, 94, 321.69, 739,
  321.75, 97, 321.84, 198.1, 356, 416.1, 418,
  433.1, 500.23, 791; 604/4, 5, 6, 28, 30

[56] References Cited

U.S. PATENT DOCUMENTS

| | | | |
|---|---|---|---|
| 4,033,345 | 7/1977 | Sorenson et al. | |
| 4,343,705 | 8/1982 | Legg | 210/651 |
| 4,425,113 | 1/1984 | Bilstad | 604/6 |
| 4,479,760 | 10/1984 | Bilstad et al. | 604/6 |
| 4,492,531 | 1/1985 | Kenji et al. | 604/5 |
| 4,631,050 | 12/1986 | Reed et al. | 604/4 |
| 4,662,829 | 5/1987 | Nehring | 417/395 |
| 4,668,399 | 5/1987 | Duggins | 210/651 |
| 4,796,150 | 9/1988 | Ramstack | 210/651 |
| 4,828,543 | 5/1989 | Weiss et al. | 604/4 |
| 4,846,787 | 7/1989 | Aall-Flood et al. | 604/5 |
| 4,886,487 | 12/1989 | Solem et al. | 604/5 |
| 4,911,703 | 3/1990 | Lysaght et al. | 604/6 |
| 4,935,002 | 6/1990 | Gordon | 604/4 |
| 5,055,198 | 10/1991 | Shettigar | 210/650 |
| 5,141,490 | 8/1992 | Fujii et al. | 604/6 |
| 5,242,384 | 9/1993 | Robinson et al. | 604/4 |

*Primary Examiner*—John Kim
*Attorney, Agent, or Firm*—Wolf, Greenfield & Sacks, P.C.

[57] ABSTRACT

A blood processor for separating blood into cellular blood components and blood fluids including means for receiving a source of blood whose components are to be separated; means, operatively associated with the means for receiving, for separating cellular blood components from blood fluids, the means for separating including means for permitting passage therethrough of blood fluids but inhibiting the passage of blood components therethrough; a pulsating pump for pumping blood from the means for receiving into the means for separating and for agitating the blood within the means for separating; and, wherein the cellular components in the blood are inhibited from blocking the means for permitting passage, thereby facilitating the movement of blood fluids through the means for permitting passage.

26 Claims, 4 Drawing Sheets

DISPOSABLE BLOOD WASHING AND APHERESIS DEVICE AND METHOD OF USING THEREOF

FIELD OF THE INVENTION

This invention relates to the processing or washing of intraoperatively salvaged or post-operatively shed blood which may be reinfused into the patient as well as for apheresis or similar applications in which certain cellular blood components are separated from blood fluids or other cellular blood components.

BACKGROUND OF THE INVENTION

This invention relates to the field of blood processors which are routinely used during a medical operation to salvage blood shed by a patient and to reinfuse or store that blood after it has been filtered and cleaned. Apheresis refers to the procedure in which a portion of the blood (plasma, platelets, etc.) is separated and either returned or disposed of and the remainder (red blood cells, white blood cells, etc.) is reinfused into the patient or off-line stored. Blood transmitted diseases, such as AIDS and hepatitis, caution against utilizing blood from third parties unless absolutely necessary. Blood washers have been developed to collect, clean and filter the patient's blood and then return it to the patient.

Typically, during an operative procedure, varying amounts of blood will be shed by a patient. This blood must be removed from the operative site to allow the physician to work, usually by a suctioning wand which aspirates blood, particulates and other fluids (such as irrigating or wash fluid) from the operation site. The suctioned blood can be either discarded or else cleaned, filtered and returned to the patient. After an operation has been performed, blood may continue to be collected through an incision in the patient's body. This blood, referred to as post-operatively shed blood, may also be cleaned and filtered and returned to the patient.

Products on the market today range from simple filtration devices which remove large particulate matter to relatively expensive hardware devices coupled to disposable components which collect, hold, and then clean and filter the blood. An example of such a device is the Cell Saver™ device marketed by Haemonetics Corporation. The Haemonetics device is comprised of a blood collection chamber and a disposable component. The Haemonetics hardware is a relatively expensive apparatus and the disposable components moderately priced. The disposable is used for a single procedure. It is then discarded after the blood has been separated into blood fluids and cellular components and then is discarded, while the hardware is used for a number of procedures again and again.

There are also many simple devices for blood processing which comprise a receptacle to receive salvaged blood and a filter which filters out particulate matters greater than the size of the filter pores. Once the blood has been filtered of particulate matter, it is then reinfused into the patient. A blood filtering device of this type is disclosed in U.S. Pat. No. 4,033,345, issued on Jul. 5, 1977 to Sorenson et al. Blood from a wound site in the Sorenson et al. device is suctioned into a receptacle and passed through a number of filters prior to reinfusing the filtered (but not separated into components) blood into a patient.

In addition to merely filtering, as is performed in simple filtering devices referred to above, it is often desirable to separate the blood components. Blood is composed of cellular blood components and blood fluids, among other things. Blood cell separation eliminates a large percentage of the plasma (as a fluid) contained in the blood, along with undesirable contaminants (such as irrigating or wash fluids and anticoagulant fluids) and returns only red blood cells to the patient. Whereas simple filtration devices referred to above eliminate large-sized particulate matter, plasma and all other components of blood are permitted to be reinfused into the patient.

Another shortcoming of a simple filtration device is that it allows undesirable micromolecular entities such as free hemoglobin and cell wall remnants that are smaller than the pore size of the filter to pass through the filter and be reinfused into the patient. The desirability of efficient filtering and washing of blood is hampered by the costs of large cell washers, such as the Haemonetics CellSaver™. The physician may then be left to the inefficiency of a simple filtering mechanism. In operative procedures in which the amount of shed blood is expected to be of a smaller volume, in the range of one or two units, the use of a conventional cell washer is not cost-effective. Simple filtration devices may be used in these circumstances, with the inherent problems discussed above, or else the blood may be disposed of and the patient reinfused with a third party's blood. This latter action increases the likelihood of a blood carried disease or immunological complication being transmitted to the patient.

Another disadvantage of presently available products is that, in the case of cell washers, personnel must be trained in the operation of the relatively complex device. Furthermore, the expense of complex cell washing devices limits their use in orthopedic and other procedures or else forces the physician, due to cost constraints, to use simple filtration systems which have the disadvantages discussed above.

In addition, some prior art devices have sophisticated controls or many moving parts which may be subject to wear or breakage. For example, U.S. Pat. No. 4,935,002, issued to Gordon, discloses a device for collecting, processing and then returning blood to a patient. One embodiment disclosed in the Gordon patent utilizes a rotating disk which performs the function of filtering and applying shearing forces to separate red blood cells from the remaining blood products such that red blood cells only pass through the filter. The Gordon device requires a motor to drive the rotating disk and discloses a microprocessor which controls various pumps which pump blood, wash solution and anticoagulant solution into the filtration system.

In U.S. Pat. No. 5,055,198 issued to Shettigar, an autologous blood recover membrane system and method is disclosed. In the Shettigar device, blood from a suction source is passed through a first filter and then, under the influence of a roller pump, blood passes through a membrane filter which separates blood fluids from red blood cells. The Shettigar device also provides for a recirculation of blood to the first filter to provide further filtering. In the Shettigar device, washing fluid is admixed with blood from the wound site prior to introduction into the first filter. A hematocrit monitor connected in line with the membrane filter will cause the blood, dependent on the hematocrit level of the blood, to either recirculate through the filter once again or to be reinfused into the patient. While Shettigar discloses a number of embodiments for his invention, the device is necessarily relatively expensive and complex.

U.S. Pat. No. 4,631,050 to Reed et al. is directed to an autotransfusion system and method. Reed discloses an autotransfusion system which consists of a first filter chamber to remove large particles which is in turn connected to an ultrafiltration unit. Blood which has been filtered by the first unit then passes through the ultrafiltration unit. In order to increase the rate at which blood fluids pass through the ultrafiltration filter, the ultrafiltration unit is pressurized on the side in which the blood fluid products are introduced, thus causing blood fluid products to pass through the filter and for red blood cells remaining on the filtration side to be siphoned off. The washed and concentrated blood cells are then reinfused to the patient. The Reed disclosure also provides for the introduction of a washing solution into the ultrafiltration cell unit to aid in the washing of the blood.

U.S. Pat. No. 4,886,487 to Solem et al. discloses a autotransfusion device in which blood is siphoned from a patient, mixed with an anticoagulant solution and then introduced into a first particulated filter where a wash solution is added. A roller pump pumps the wash solution and blood through a second filter which separates blood fluids from red blood cells and returns the red blood cells to the patient. A vacuum source is required to withdraw the suctioned blood from the patient site into the first filter and a roller pump is required to pump the filtered blood through the second separation filter. All of the above prior art devices require various controls and motors to cause filtration and separation of blood components.

SUMMARY OF THE INVENTION

The disposable blood washer of the present invention includes one or more hollow fiber cell or other suitable separators which separate red blood cells from blood fluids. The separator is attached to a pulsatile pump which may be of a type disclosed in U.S. Pat. No. 4,662,829 and sold under the name Arthro-flo™ and assigned to the assignee of the present invention. The Arthro-flo™ pump may be modified, by methods well known to those skilled in the art, to change its speed of operation and/or volumetric capabilities. The pulsatile pump provides a low pressure membrane source for driving blood through the separators as well as providing, an agitating action to keep blood cells from adhering to the filter surfaces. Thus, the blood cells remain in a suspended state within the fibers to assist in the removal of blood fluids through the filters. In constant or steady pumped or gravity flow systems, by comparison, blood cells tend to adhere to the fiber surfaces and inhibit the flow of blood fluids out through the hollow tubes. This reduces the efficiency by which blood fluids may be separated and removed from the red blood cells.

The pulsatile pump may be driven from any pneumatic source readily available in the hospital and is self regulated by resistive forces built into the pump structure (the inlet, outlet conduits and the pumping chamber itself) to pump the blood through the separator or separators. The pump's capabilities maybe either pre-set or adjustable, as desired.

In the present invention, washing fluid may be admixed with the blood prior to its introduction into the pulsatile pump and subsequently the separator(s). It is important that the ratio of washing fluid to blood be closely regulated to provide a consistent desirable end product for infusion. When the blood is already highly diluted little, if any, washing fluid needs to be added to the blood. This can occur during an operative procedure in which the physician used a large amount of washing fluid to clear or clean the operative areas. If however, the blood salvaged is relatively undiluted, such as when blood has been suctioned directly from a bleeding wound site, more washing fluid is required to be admixed with the salvaged blood.

The present invention includes a control valve mechanism which may be movable to a number of positions, the positions corresponding to the amount the control valve is opened and the amount of wash fluid being admixed with the incoming blood. A pointer is attached to the control valve and points to a color chart. The color chart preferably has two or more bands of colors. The colors on the chart correspond to colors the blood would appear to take dependent upon the amount non-blood fluids, such as washing fluids, admixed with the blood. Highly diluted blood is a translucent red-orange color. Less diluted blood appears more red translucent in color and undiluted blood appears purple and opaque.

When the pointer is moved to point to the red-orange (most dilute) color band, the valve is closed or virtually closed so that very little, if any, wash fluid is added to the blood entering into the pulsatile pump. When the blood is in the red range (indicating a moderate amount of washing fluid having been admixed at the operative site with the blood), the valve controlling the amount of wash fluid will be opened up slightly to allow more washing fluid to enter. When the blood appears purple opaque (indicating virtually undiluted blood), the pointer is turned to the purple band which opens the valve almost fully to allow full flow of wash fluid to be admixed in a predetermined proportion with the blood and into the pulsatile pump. A chamber positioned adjacent the valve allows the user to more accurately match the blood color with the color chart.

One-way valves are located distally of the blood input bag or receptacle and the wash fluid bag receptacle to prevent any back flow or intermixing of blood with saline wash solution. After the blood admixed with the saline wash solution has been pumped through the separator(s), blood fluids will be siphoned off into a waste bag and red blood cells passing through the hollow fiber tubes will enter into a blood collection bag which may then be either directly reinfused into the patient or disconnected from the device and stored. Upon completion of the procedure, the entire blood processor may be disposed of, thus eliminating any potential contamination. The blood processor is sufficiently inexpensive and self-contained that it can be economically disposed of.

It is among the general objects of the present invention to provide an improved, disposable device which both filters and washes salvaged or post operative blood products.

It is yet another object of the present invention to provide a disposable blood washer which is relatively inexpensive and has great ease of use, allowing it to be used by a variety of hospital personnel without extensive prior training. The present invention provides a blood washer which is disposable and is simple to operate by even those without a great deal of training.

It is another object of the present invention to provide an improved disposable blood washer which utilizes a pulsatile pump to pump the blood and wash fluid admixture through one or more separators while preventing a build-up of cells on the filters to achieve maximum efficiency of separation of blood fluids and blood cell components.

It is a further object of the present invention to provide a disposable blood washer which utilizes a simple color coded control or valve to meter the amount of wash fluid to be introduced into the pulsatile pump which requires only that the operator match the color of the blood to be infused with a color band or chart on the blood washer.

Another object of the present invention is to provide a disposable blood washer which may be substituted for both blood filtering devices which provide no washing function and very expensive blood separating cell washer systems for even low blood recovery volumes.

DESCRIPTION OF THE DRAWINGS

The foregoing and other objects have advantages of the invention will be appreciated more fully from the accompanying drawing.

DESCRIPTION OF THE PREFERRED EMBODIMENT

Figure 1:
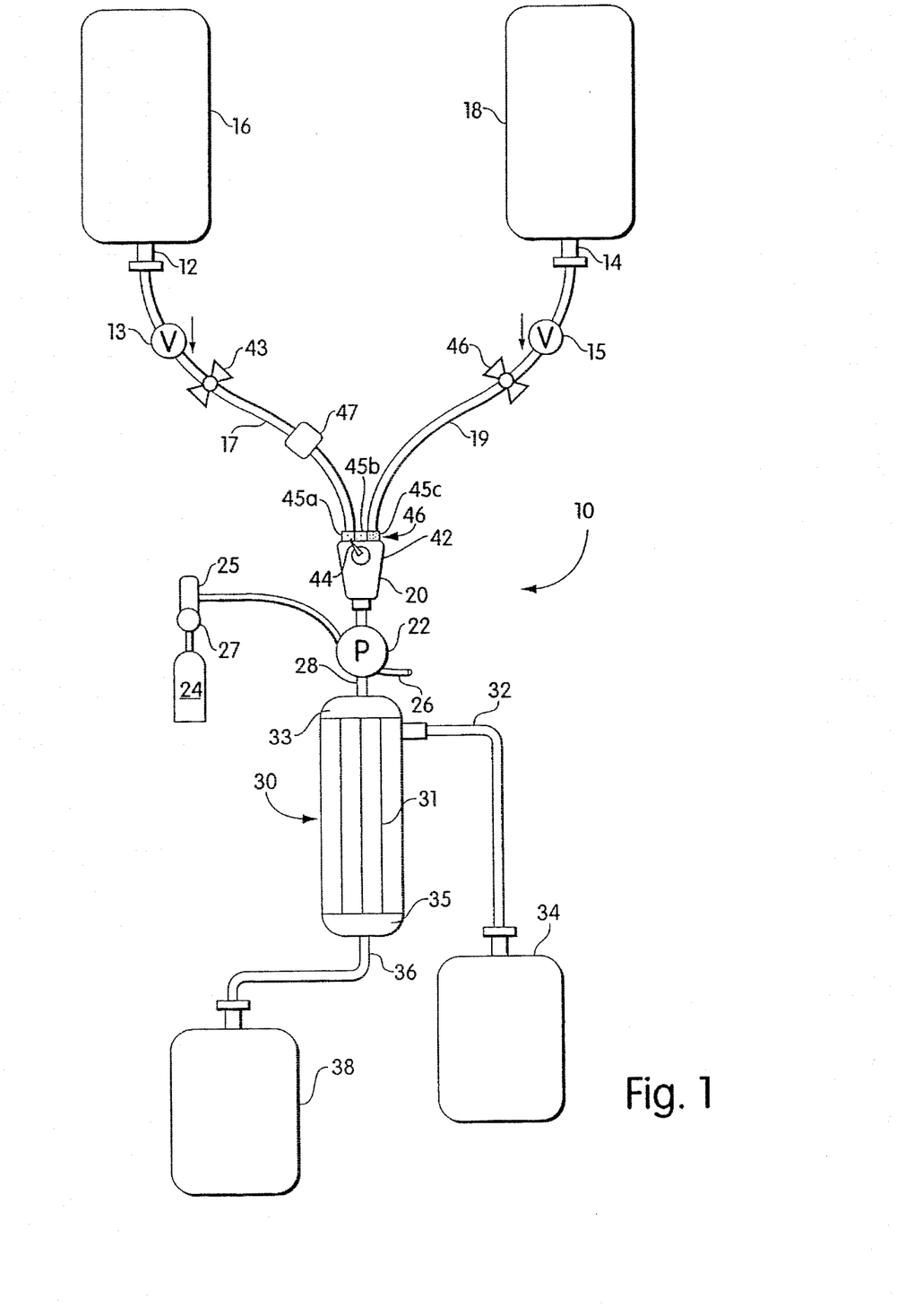
FIG. 1 is an illustration of the first preferred embodiment disposable blood washer.

Referring now to FIG. 1, the disposable blood washer 10 includes a blood spike port 12 and a washer fluid spike port 14 each of which may be connected respectively to a source of blood (the components of which are to be washed or separated) and wash fluid which may be utilized to assist in the "washing" of the blood. Distally of each of the spike ports 12 and 14 are one way valves 13 and 15 which act to prevent a back flow of blood or wash fluid into the blood container or the wash fluid container. Each of the one way valves 13 and 15 are connected by lines 17 and 19 to a Y-connector valve housing 20. The function and operation of the Y-connector valve housing 20 will be discussed below. The Y connector valve housing 20 is connected by line 21 to a pulsatile pump 22. The pulsatile pump chosen is a low pressure, pneumatically driven pulsatile membrane pump that produces a fixed upper internal static pressure below the threshold that would be harmful to red blood cells and to other cellular components contained in blood. The pulsatile pump is connected to a low pressure pneumatic source as shown as 24 which acts to drive the pump. The upper limit to which the pump will be activated is controlled by the design of the pump and also by the addition of an external regulator 27 known to those skilled in the art which is connected at the source of the pneumatic source 24. A pneumatic source connector 25 connects the pulsatile pump to the low pressure pneumatic source 24 through line 29. Furthermore, an exhaust 26 acts to exhaust the gas from the low pressure source at the pump body 22. A pump which is suitable for use in the present invention is a pump known as the Arthro-flo™ pulsatile pump which is described in U.S. Pat. No. 4,622,829 and is assigned to the assignee of the present invention, the disclosure of which is incorporated by reference herein. A outlet 28 from pump 22 is a line or conduit which is connected to a filter or separator 30.

Figure 3:
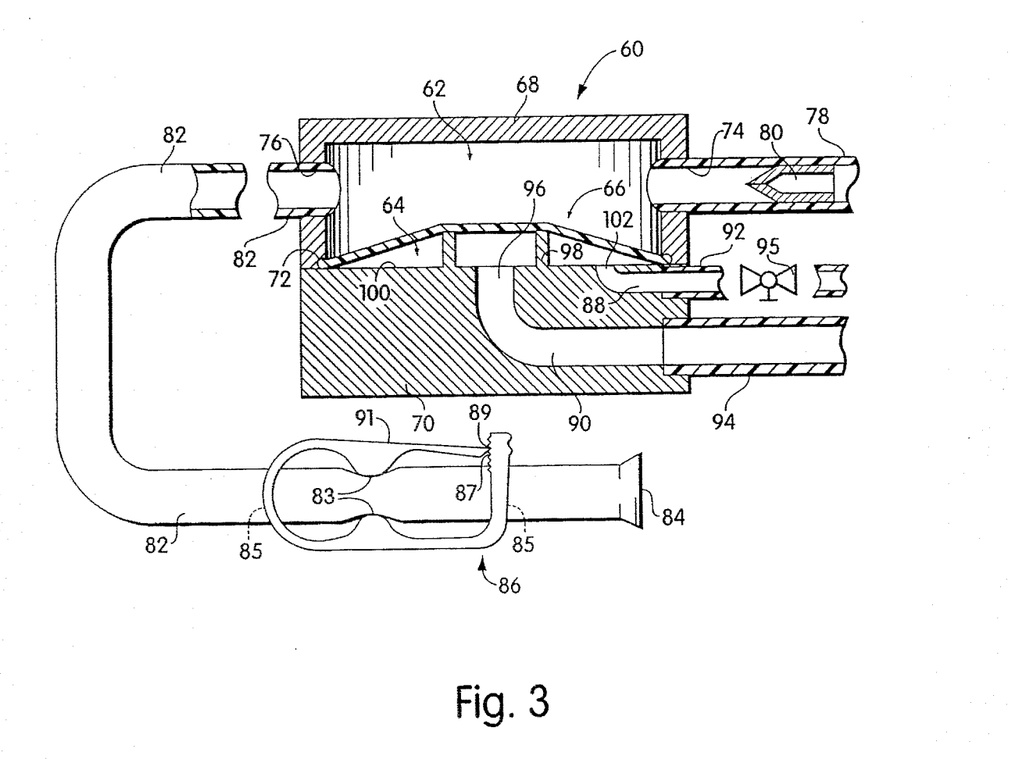
FIGS. 3, 4 and 5 illustrate the structure and operation of one embodiment of the pulsatile pump of the present invention.
Figure 4:
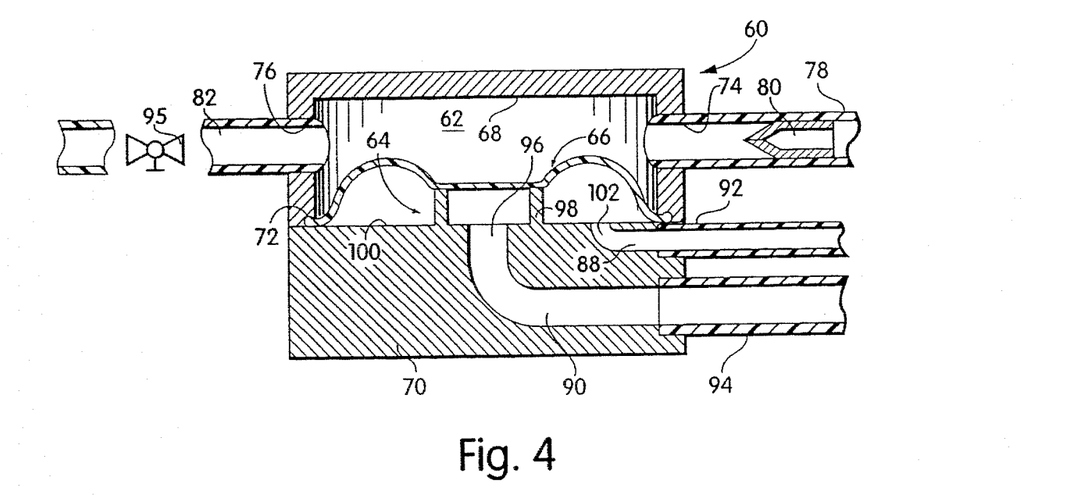
Figure 5:
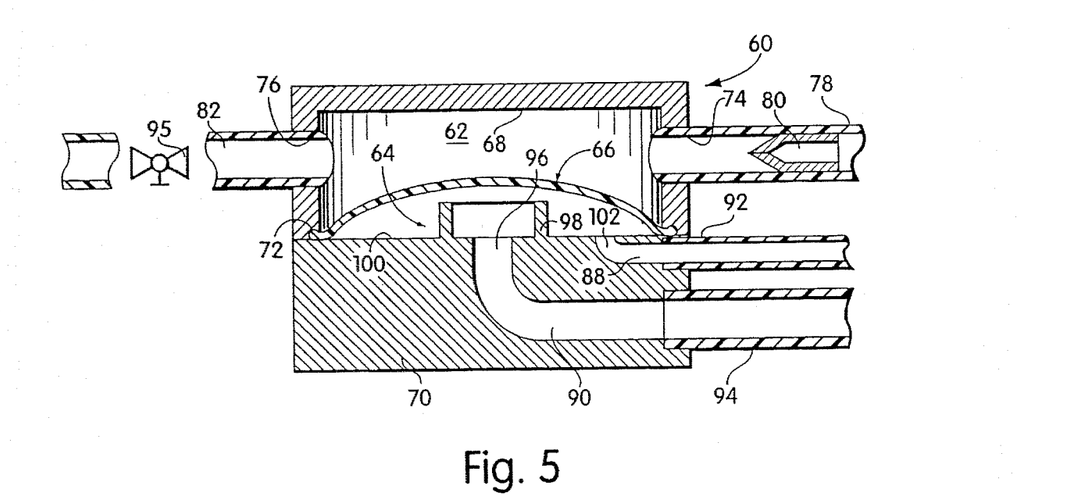

While the disclosure of U.S. Pat. No. 4,622,829 is incorporated by reference, the basic operation of the patentable pump is described as follows. FIGS. 3–5 illustrate, diagramatically, an embodiment of the invention in which the pump 22 of FIG. 1 is driven by positive pneumatic pressure. As shown in FIG. 3, the device includes a housing 60, the interior of which is divided into a variable volume pumping chamber 62 and a driving chamber 64, the chambers 62, 64 being defined and separated by a flexible, resilient member 66, such as an elastic diaphragm. The housing 60 may be formed in two sections 68, 70. The flexible resilient member 66 preferably is captured between the housing sections 68, 70 when the device is assembled. The periphery of the flexible resilient member may be provided with an enlarged rim 72 which can be received in a receptive groove formed in one or both of the sections 68, 70 to cooperatively grip the rim 72. The housing sections 68 and 70, and the periphery of the flexible resilient member 66 are sealed to assure hermetic isolation between the chambers 62, 64 as well as a complete seal to the atmosphere.

The housing 60 includes a fluid inlet 74 and a fluid outlet 76 leading to and from the pumping chamber 62. The inlet 74 is connected by a tube 78 to a source of the fluid which is to be pumped such as, in the present invention, the blood and saline wash fluid containers, 16 and 18, respectively. The device also includes means for maintaining unidirectional flow along the flow path defined by the inlet 74, pumping chamber 62 and outlet 76 and, to that end, a check valve 80 may be placed along the flow path, preferably in the inlet conduit 78. Although an additional check valve may be placed in the outlet line, the manner in which the device operates enables an outlet check valve to be omitted, as will be described.

The outlet 76 of the housing 60 is connected to an outlet tube 82 which may terminate in an outlet nozzle 84. A throttling valve, indicated generally at 86, is interposed along the flow path defined by the outlet tube 82 and nozzle 84. The type of throttling valve may vary with the intended use of the device. The throttling device may take the form of a simple adjustable clamp, as shown in FIG. 3, which is fitted onto the flexible tubing 82. Such a clamp can be located at the nozzle or at a more upstream location along the tube 82 as desired. In other embodiments the throttle valve may take other forms and may be incorporated into a hand held nozzle so as to be operated conveniently by the user. The clamp is a commercially available clamp formed from a unitary plastic defining a pair of compression pads 83 which grip and squeeze the flexible tube 82. The tube extends through apertures 85 formed in the clamp 86. One end of the clamp includes a ratchet surface 87 which cooperates with a relatively sharp edge 89 of another leg 91 of the clamp to lock the clamp in any of a variety of positions. The various positions in which the clamp may be locked determine the degree to which the tube 82 is throttled by the pads 83.

The pumping action is effected by oscillations of the elastic diaphragm 66. The device includes a two-stroke mode of operation, including an ejection stroke and a filling stroke. In the ejection stroke, diaphragm 66 is caused to flex to decrease the volume of the pumping chamber 62, applying pressure to the fluid in the chamber 62. During the ejection stroke, fluid is caused to flow from the pumping chamber 62 through the outlet tube 82 and is dispensed from the nozzle 84. Reverse flow is prevented by the check valve 80. As described below, the ejection stroke is terminated abruptly and in a manner to enable the elastic diaphragm 66 to return to its starting position in which the volume of pumping chamber 62 re-expands to its original volume. The re-expansion of the member 66 defines the filling stroke and causes fluid to be drawn from the fluid source through the inlet tube 78 and check valve 80 to the pumping chamber 62, in readiness for the next pumping stroke.

The flexible, resilient member 66 is constructed and mounted in the housing 60 so that it can oscillate under the influence of positive pneumatic pressure applied to the driving chamber. To that end the device includes an air inlet passage 88 and air outlet passage 90. Inlet passage 88 is connected to a source of air or other appropriate gas under pressure by an air inlet tube 92. Exhaust from the air outlet passage 90 may be communicated from the driving chamber by an exhaust tube 94. The air exhaust passage 90 leads from an exhaust port 96 which, in the illustrative embodiment, is located in registry with the center of the elastic element 66. Exhaust port 96 is arranged to communicate with the driving chamber 64. The diaphragm 66 is normally biased toward the exhaust port 96 so as to seal off the exhaust port from the driving chamber 64. In the embodiment illustrated in FIGS. 3–4 the bias is accomplished by the elasticity of the diaphragm 66 and by providing a bearing member such as an upstanding wall 98 which surrounds the exhaust port 96 and over which the elastic diaphragm 66 is stretched. In this configuration of the device the height and location of the wall 98 is selected with respect to the manner in which the peripheral rim 72 of the diaphragm 66 is held in place. In the embodiment shown, the elastic diaphragm 66 is stretched into a dome shape and is maintained under an elastic tension which biases the diaphragm 66 toward the exhaust port 96 to close the port 96. Thus, in the embodiment shown in FIGS. 3–4 the driving chamber 64 may be considered as somewhat annularly shaped, being bounded by the wall 98, the surface of the elastic diaphragm 66 and the surface 100 of housing section 70. The air inlet passage 88 communicates with the driving chamber 64 at an air inlet port 102 which opens through the wall surface 100 of the housing section 70.

The operation of the foregoing embodiment is illustrated with further reference to FIGS. 4 and 5. The system first is primed so that the fluid which is to be pumped completely fills the flow path from the reservoir, through the inlet tube 78, pump chamber 62 and outlet 82, 84. Priming is accomplished easily by opening the throttle valve 86 and allowing the liquid to flow by gravity or under light pressure through the system. Once primed, the throttle valve is closed in readiness for pumping operation. In the ejection stroke of the cycle pneumatic pressure is applied at air inlet tube 92. As the pressure builds up within the driving chamber 64 the elastic diaphragm 66 expands to form a domed annular configuration. The pressure built up within the driving chamber 64 is applied, through the diaphragm, to the fluid in the pumping chamber 62 thereby ejecting fluid through the outlet 76. The volume of fluid pumped in the ejection stroke is equal to the difference in volume in the driving chamber from its relaxed (FIG. 3) position to its position of maximum expansion (FIG. 4). The maximum expansion, as well as the force in the ejection stroke can be controlled and varied as will be described further below.

The ejection stroke continues as long as the flexible resilient element remains biased in sealed relation against the exhaust port 96. In the embodiment shown in FIGS. 3–5, in which the member 66 is an elastic diaphragm, biasing force is created by the inherent elasticity of the diaphragm and the manner in which it is stretched over the rim of the wall 98 which surrounds and defines the exhaust port 96. The central portion of the diaphragm which makes the seal against the rim of the wall 98 maintains that seal until the remaining portion of the diaphragm 66 has been flexed and expanded to a point in which the opening force applied to the central portion of the diaphragm by the expanding peripheral portions of the diaphragm exceeds the biasing force. The central portion of the diaphragm 66 is maintained in seated sealed relation against the rim of the wall 98 not only under the influence of the bias of the elastic diaphragm but also under the influence of a pulse of increased pressure applied to the fluid in the pumping chamber. Thus, as the diaphragm expands into the annular dome-shaped configuration illustrated in FIG. 4 the pressure pulse applied to the liquid in the pumping chamber forces the central portion of the diaphragm more firmly into seated engagement on the rim of the wall 98. That additional pressure enables the diaphragm to expand to the annular domed configuration shown in FIG. 4, in which the central portion of the diaphragm remains depressed, in a dimpled configuration with respect to the annular expanding portion of the diaphragm during a portion of the ejection stroke. In this regard it should be noted that the impedance in the outlet line also has an effect on the timing of the unseating of the diaphragm from the air outlet port. The impedance of the outlet should be great enough to allow sufficient pressure to build up within the pumping chamber so as to maintain the central portion of the diaphragm in sealing engagement on the outlet port for a time sufficient to enable a desired volume of liquid to be pumped during the pumping stroke. As the ejection stroke nears completion the stretched diaphragm abruptly unseats the central portion of the diaphragm from its sealing engagement with the rim of the wall 98.

At the moment that the sealed, central portion of the diaphragm abruptly unseats from the rim of the wall 98, as shown in FIG. 5, the elastic diaphragm immediately assumes the more uniform dome shape suggested in FIG. 5 under the influence of the equalization of the internal elastic forces in the diaphragm. The internal elastic forces within the diaphragm 66 cause the diaphragm to contract, which draws the diaphragm down into sealing engagement with the rim of the wall 98.

During the elastic contraction of the diaphragm, the air which was in the driving chamber 64 is exhausted immediately and rapidly through exhaust port 96, air outlet passage 90 and exhaust tube 94. The immediate and rapid exhaust from the driving chamber 64 is assured by providing substantially larger outlet passages than those associated with the air inlet. Thus, outlet port 96, air outlet passage 90 and exhaust tube 94 are arranged so as to prevent a minimum of back pressure which might impede rapid exhaust of air from the driving chamber.

In order to assure that the diaphragm will collapse rapidly it is important that the impedance in the air outlet line is substantially less than that in the air inlet. This may be accomplished by selectively proportioning the flow areas of the air inlet and air outlet. If desired, a fixed or variable flow restrictor (suggested diagrammatically at 95 in FIG. 3) can be placed at the air inlet. Use of a flow restriction device 95 at the air inlet also prevents development in the driving chamber of too high pressures and inlet flow rates which could stall the diaphragm in the open, domed configuration. The flow impedance in the fluid line 82 outlet should be greater than the flow impedance at the fluid inlet 74, including the effect of the inlet check valve 80.

As mentioned above, it is not necessary to use a check valve in the fluid outlet. During the filling stroke, the contraction of the diaphragm reduces the pressure in the pumping chamber. Fluid is drawn in through the inlet 74 and check valve 80 at the inlet. Although there is no check valve in the outlet line the filling stroke does not draw liquid back into the pump chamber. That is believed to result from the inertial effect of the liquid flowing through the outlet during the pumping stroke. When the diaphragm abruptly unseats and substantially immediately begins to contract in a filling stroke, the action is too abrupt to decelerate and reverse the flow of the liquid flowing in the outlet tube. Additionally the inertial effect of the liquid in the outlet tube is affected by the length of the outlet tube as well as the impedance of the inlet check valve. The length of the outlet tube preferably should be great enough to present a substantial impedance to reverse flow. A tube at least one foot long and as long as about eight feet or more is satisfactory.

The throttling control 86 affects the frequency of pulsation as well as the pulse strength (the velocity of the emitted fluid jet). As the throttle valve is opened the frequency of the pulses increases and the velocity of the pulses increases.

Operation of the device is controlled manually by the user by controlling the throttle valve 86. When the valve is closed there is no flow through the system. As the valve is opened, the resulting differential pressure across the diaphragm initiates the pumping cycle. The cycle will repeat automatically and continuously as long as the throttle valve remains open. The delivery rate, exit velocity and pulse frequency increase from zero when the valve is fully closed to progressively higher values as the valve is fully opened. Other variations of the pump embodiment of FIGS. 3–5 are described in U.S. Pat. No. 4,622,829, referred to above. With the pulsatile pump as described in the foregoing patent and further described herein, by controlling back pressure through the pump (back pressure being the resistance of the blood or blood/saline admixture to move through and out the fibers), by varying the degrees of opening and closing, and the opening of the inlet and outlet of the pump, the degree of filtering may be controlled as desired.

Thus, it will be apparent to one of ordinary skill in the art that the pulsating pump 22, as described herein and in U.S. Pat. No. 4,622,829 which has been incorporated by reference, is an open loop pump which operates automatically and continuously in response to an applied positive or negative pressure differential. The open-loop pump 22 does not require a microprocessor and associated sensors to control the filling and ejection strokes of the pump or to shut down the pump when excessive pressures are reached which can damage red blood cells.

Thus, in operation, the pump 22 operates to receive fluids through line 21 and to push them through the pump and through line 28 to the filter or separator 30. Although one filter is shown in the drawing, it may be desirable to use more than one filter in order to increase the separation of blood fluid components from blood cells. The filter 30 may be a hydrophilic hollow-fiber cell separator, or may be of the hydrophobic variety. The difference between hydrophobic and hydrophilic fibers is that hydrophobic fibers generally require a prime unit of saline solution to "wet" the fibers while with hydrophilic fibers no such primping may be required. Such cell separators are available in many sizes and varieties and provide for specific blood separation applications. Filter 30 comprises a number of hollow tubes running longitudinally through the filter 30. One such illustrative tube 31 extends from the inlet 33 of the separator or filter 30 to the distal end or exit 35 of the separator or filter 30. Each of the hollow tubes is perforated with holes which allow the passage of blood fluids but do not permit the passage of blood cells there through. Thus, when blood enters the filter 30, the cellular material is constrained to travel from the inlet 33 to the outlet 35 without escaping, while blood fluids and other smaller materials escape through the perforations in the hollow fiber walls and collected as described below. Fibers usable in the filter 30 are available from Mitsubishi Rayon in a product known as Polyethylene Microporous Hollow Fiber Membranes. Other suitable hollow fiber microporous membrane separations and filters are disclosed in copending Robinson et al. application Ser. No. 07/852,940, filed Mar. 13, 1992, entitled "Blood Pumping and Processing System", assigned to the assignee of the present invention. Further suitable separators are disclosed in U.S. Pat. No. 4,911,703, issued on Mar. 27, 1990, to Lysaght et al., as described in col. 13, line 18 through col. 14, line 4, as well as in U.S. Pat. No. 4,828,543, issued on May 9, 1989, to Weiss et al.

The hollow fibers of the filter 30 are porous and thus have a number of holes or perforations for the passage therethrough of fluid materials contained in the blood. In gravity feed or steady pressure systems (such as would be experienced when a steady flow pump induces the flow of blood through such filters) there is a tendency to draw cellular materials to the holes or perforations, which inhibits the passage of fluid out of the hollow fibers, and thus filtering capacity is comprised. With the use of the pulsatile pump 22 of the present invention, however, the pulsating action of the pump keeps the blood and thus the cellular material in the blood moving and suspended within the hollow fibers. This decreases the tendency of cellular material to block the holes or perforations in the fibers and increases the efficiency with which cellular components are separated from fluid materials of the blood. The pulsatile pump 22 provides sufficient pressure to overcome normal flow resistancies of the cell separator hollow fibers, which promotes the flow of blood through the filter or separator at a velocity greater than that which would be obtainable in a gravity feed system. Thus, the use of the pulsatile pump has an advantage over both a gravity feed system as well as a steady flow pumped type system. Other types of known separators, such as flat plate separators, may be used with the present inventions. In such filters, the agitating action of the pulsatile pump will prevent cellular buildup on the plate surfaces, as with the hollow fiber embodiment described above.

Blood fluid materials, such as plasma, irrigation fluid and anticoagulant fluid, which may have been present in the operative site, and wash fluid are removed by the filter or separator 30 and are passed through tube 32 to a waste bag 34. Cellular components such as red blood cells, however, continue through the hollow tubes and exit at the outlet 35 and will be removed by line 36 to a blood collection bag 38. When the processing of blood is completed, either after the termination of the operation or at any time as desired, the blood collection bag may be removed for either reinfusion into the patient or for storage for later use or any other suitable use.

An additional feature of the present invention is a simple regulator 42 which is incorporated into the valve housing 20. The regulator serves to regulate the amount of wash fluid which may be admixed with the blood prior to its entry into the pulsatile pump 22. In conventional blood treatment procedures, as is well known to those skilled in the art, mixing a certain amount of wash fluid (which may be a saline or other blood compatible solution) with the blood to some extent dilutes the blood and allows the separation to proceed at a more efficient rate than if whole blood were pumped through the filtration system. However, as is well known to those skilled in the art, it is necessary to control the amount of wash fluid added to the blood so that there is not an excessive amount of fluid which would impair the efficiency of the filtration system. Likewise, a less than adequate amount of wash fluid would not sufficiently dilute the blood to aid in the washing of the blood materials. An excess of wash fluid may also require reintroduction of the blood mixture for a second separation so that the hematocrit level of the separated blood is at the desired level for reinfusion.

Whereas in the prior art many somewhat complicated mechanisms (such as hematocrit level detections) have been used to apportion the mixture of the blood and the wash fluid, in the present invention a simple color chart serves to indicate to even an untrained operator the correct amount of wash fluid to be introduced and mixed with the blood. Blood which has been removed from a surgical site is not uniform in color (reflecting relative dilution of the blood) from patient to patient nor is it uniform during even a single surgical operative procedure. This is because blood will be suctioned from the surgical site at various points during the procedure. At times during the procedure, the physician may spray or otherwise introduce irrigation fluid into the surgical area to clean the operative site or for other purposes. In addition, anticoagulant fluid may be introduced at the site to prevent coagulation and formulation of blood clots at the surgical site. At other times during the operation, such as when a blood carrying vessel like a vein or artery may be cut, the blood suctioned off will be relatively undiluted. Therefore, when the physician has removed, by suction or otherwise, a given amount of blood from the surgical site, the relatively diluted state of the blood will vary from patient to patient and will vary even during the same operative procedure. In instances where the blood is already highly diluted with wash fluids and other fluids, it may be unnecessary to add much, if any wash fluid to make the admixture suitable for introduction into the filter 30. In instances, however, when the blood is relatively undiluted, it may be necessary for maximum efficiency of the filter 30 to dilute the blood with a greater amount of wash fluid then in the case of relatively diluted blood. Relatively undiluted blood appears purple and opaque in color whereas blood diluted to a moderate extent appears to be more red translucent. Blood which is highly diluted appears to be red-orange translucent.

The regulator 42 of the present invention includes an indicator pointer 44 which is connected to the valve 21 which controls the amount of wash fluid which is to be introduced and mixed with the blood. Valve 21 may be any of commercially available rotary (faucet-type) valves or even slide valves or stopcocks which may be adjustably opened or closed dependant on the position of a valve handle or control. A color chart strip 46 is positioned in the vicinity of pointer 44 so that the indicator pointer 44 may be moved manually across the strip 46. The strip 46 may be comprised of two or more colors corresponding approximately or exactly to the colors of the blood contained in the blood container in the blood collection bag 16. As shown in FIG. 1, the color strip 45a may be colored translucent red-orange to correspond to a highly diluted blood source, the color strip 45b may be colored red to correspond to a moderately diluted blood source and the color strip 45c may be colored purple to correspond to relatively undiluted blood source. As an aid to the user, the blood line 17 may have a chamber 47 into which blood enters prior to entering the valve 21. The chamber, which may be suitably of rectangular shape, is preferably transparent and may be used to present to the user an accurate view of the color of the blood so that matching with the appropriate color on chart 46 is facilitated. If the pointer 44 is moved manually by the operator to the position corresponding to color strip 45a, this action serves to close down the valve which controls the entry of wash fluid into the valve body 20. This position would correspond to a complete or almost complete shutting of the valve 21 to prevent any wash fluid into the valve body 20. As the pointer 44 is moved from the position to color strip 45a to color strip 45b the valve would be open to an extent to allow a predetermined amount of wash fluid to enter in to the regulator 20 and be mixed with blood from the blood collection container 16. As the pointer 44 is further turned to match with the color strip 45c the valve would at that position would be open to its fullest extent to allow the maximum amount of wash fluid to enter in to the valve to mix with the blood from the blood collection container 16. In the preferred embodiment, the largest openings of the valve 21 corresponds to a flow of wash fluid into valve body 20 approximately equal to the flow of blood from blood source 16.

Thus, in operation, a container of blood 16 which may have been aspirated from the surgical site is connected through spike 14 to conduit 17 leading to the valve body 20 and hung on an IV pole. A bag of saline or wash fluid solution is hung on the IV pole and is connected through spike 14 to line 19 to the valve body 20. It is assumed that the pulsatile pump 22 has been connected through the pneumatic source connector 25 to a pneumatic source 24 without, however, activating the start of the pump at this juncture. Next, the operator observes the color of the blood to be processed and adjusts the indicator pointer 44 so that the color of the blood closely matches the color on the indicator strip 46 which the pointer 42 is pointing to. This matching opens up valve 21 to allow the flow of the proper amount of wash fluid to be admixed with the blood in a predetermined proportion. One way valves 13 and 15 prevent the flow of blood from the bag 16 to the wash fluid bag 18 and vice versa. They also prevent leaks out of the spike ports 12 and 14 in the absence of a bag attached to either port and prevent back flow of blood or wash fluid due to the action of the pulsatile pump 22. In the next step, the pulsatile pump is connected to a pneumatic source and a regulator valve 27. Clamps 44 and 46 which prevent the flow of either blood from the container 16 or wash fluid from the container 18 to the valve by then opened and blood and wash fluid (if the valve 21 is set to introduce wash fluid) will then flow through the valve body 20 and into the pulsatile pump 22. When the pulsatile pump 22 is activated, as described in U.S. Pat. No. 4,662,829, blood or a admixture of blood and wash fluid will be pumped in a pulsatile flow fashion through the hollow fiber of the cell separator of filter 30. Separated blood cell components will enter the blood bag 38 through line 36 while waste fluid will enter waste bag 34 through line 32. The pulsatile pump by design is self-regulating and will provide maximum flow when downstream resistance is low or automatically compensate to decrease the flow when the downstream back pressure is high. When downstream pressure exceeds the design limits of the pump, the pump 22 will stop pumping until the downstream pressure is reduced below the threshold design limit pressure level. When all the blood in the bag 16 has been processed, the unit is disconnected from pneumatic source 24, from the wash fluid container 18 and the entire device is disposed of.

Figure 2:
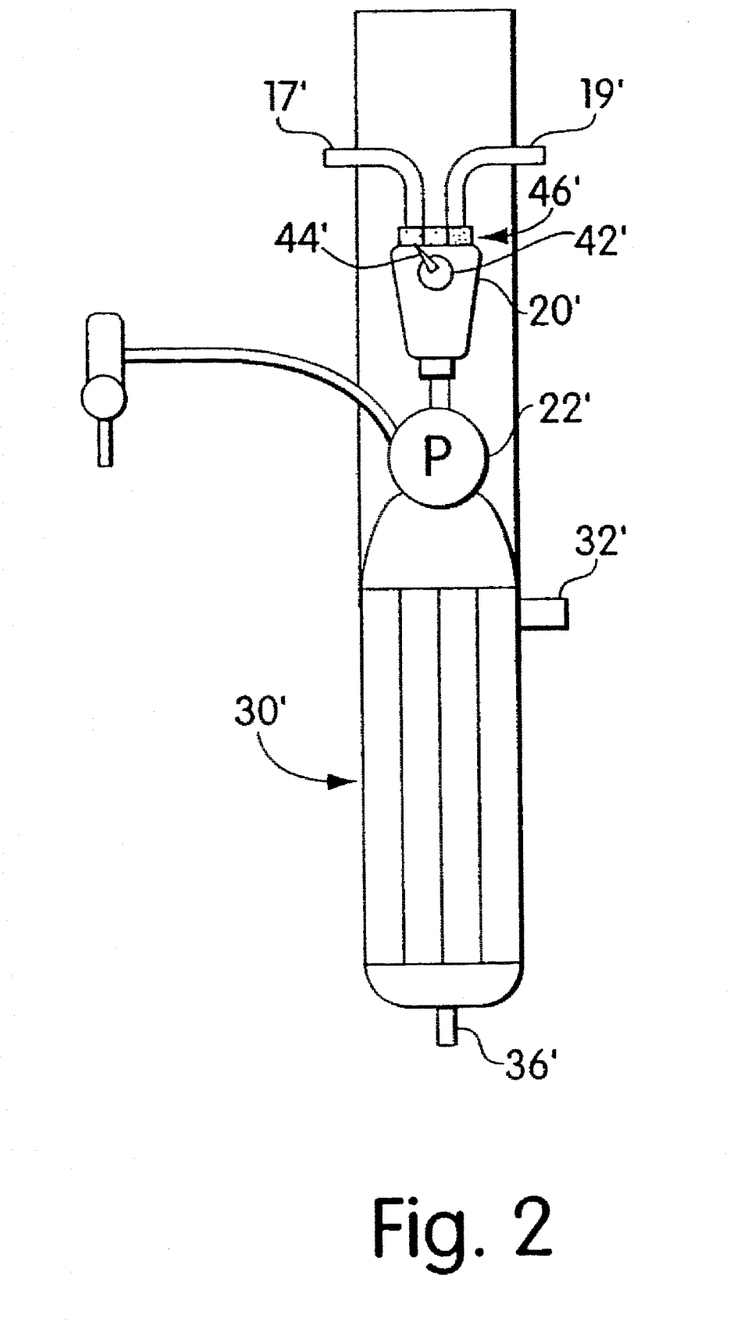
FIG. 2 is an illustration of the second preferred embodiment of the disposable blood washer.

In a second embodiment, to simplify the structure and cost of a device constructed in accordance with the present invention, the pump is integrated with the filter. In yet another embodiment, the valve housing, the regulator and the pulsatile pump may be formed in a unitary housing which may be readily attached to existing IV poles and to sources of blood and wash fluid. This embodiment serves to decrease cost of construction of the device and to ease the disposal of the unit due its smaller size. FIG. 2 shows a modified embodiment of the present invention in which the membrane filter 30' is integrally formed with the pump body 22'. A pump body 22' is of the same construction as described in U.S. Pat. No. 4,662,829 but its outlet is integrally formed and sized to the inlet 35' of the membrane filter 30'. In addition, the valve body 20' is mounted on the pump with the valve controls described in reference to FIG. 1 above. Ports 17' and 19' respectively receive connections to sources of blood and saline solution. Outlet 36' is connected to a blood bag for containing separated blood cells and outlet 32' receives blood fluid materials removed from the blood as previously described with reference to the embodiment of FIG. 1. Elements 42', 44' and 46' correspond in function and structure to their counterparts 42, 44 and 46 in the embodiment of FIG. 1. In use, when a unit of blood is to be processed, the blood source will be connected or fixed to a IV pole by suitable means and the ports 17' and 19' connected respectively to sources of blood and wash fluid. The outlets 36' and 32' will be connected respectively to the blood bag and to a waste bag. As with the embodiment of FIG. 1, the pulsatile pump will be connected to the pneumatic source and the pointer 44' moved to the appropriate section representing the color of the blood which is to be processed. When all the blood in the blood bag is in process, the unit 10' will be removed from the IV pole and be disposed of.

As will be appreciated by one of ordinary skill in the art, the systems illustrated in FIGS. 1 and 2 provide a circuit for conducting blood from a blood source to the pump and through the separator, and a circuit for introducing a wash fluid into the blood conducting circuit. In the intergral disposable housing system illustrated in FIG. 2, the blood conducting circuit includes port 17', Y-connector 20', pump 22' and separator 30'. The wash fluid introducing circuit includes port 19' and Y-connector 20'.

By use of the simple mechanical valve or regulator, desired amounts of washing fluids can be easily controlled even by untrained operators. The present invention fills the void between expensive blood processing units and simple filtration units and has applications in plasmapheresis, platelet apheresis and other procedures in which is desirable to selectively wash unwanted materials or just to separate blood components. The present invention is adaptable to any blood collection container (interoperative autotransfusion collection devices, post-operative autotransfusion collection devices, and canisters) in which there is a spike port. In addition, it adapts to any saline bag or other container that also has a spike port. All of the components of the present invention, the valve body regulator, the pulsatile pump and the separator(s) may be suitably combined into a small-sized housing which can be easily handled and disposed of when the blood separation procedure has been completed. Use of more than one separator or filter, while increasing the expense of the device, allows for greater proportions of removal of unwanted blood or fluid materials. In addition, the amounts of blood fluid or other materials which may be removed may be increased by increasing the number and/or diameter of fibers contained in each of the filters. Thus a number of different modifications to the present invention are possible if it is desired to achieve specific results in removal of blood fluid materials from blood.

While the apparatus of the present invention has been described primarily as useful in separating plasma from cellular blood components, with the choice of suitable filters other separators are feasible. For example, while the invention has been described as having one or two filters of the same or a similar type to filter platelets, it is also possible to utilize a series of different filters, mounted in tandem or otherwise (such filters being well known to those skilled in the art) which will allow the operator to selectively extract plasma, platelets, white blood cells, or red blood cells as desired.

From the foregoing, it will be appreciated that there has been described an improved disposable blood washer which combines the blood washing capabilities of much more expensive cell washers with the relative inexpensive costs of blood filtration systems, which is totally disposable and which has great ease of use due to its simple pump which eliminates electrical and mechanical connections. The color matching valve allows operation of the device even by untrained operators.

While the invention has been described in terms of the preferred embodiment, it should be understood, however, that the foregoing description of the invention in intended merely to be illustrative thereof and that other modifications and embodiments may be compared to those skilled in the art without departing from its scope. Having just described the invention, what is desired to be claimed by Letters of Patent is:

I claim:

1. A blood processor for separating blood into cellular blood components and blood fluids comprising:

a circuit for conducting blood whose components are to be separated;

a separator included in said circuit for conducting blood for separating cellular blood components from blood fluids;

an open loop pneumatically driven pulsating pump fluidly connected to the circuit for conducting blood that pumps blood along said circuit for conducting blood and into said separator without reversible flow to agitate the blood within said separator so that the cellular components in the blood are inhibited from blocking movement of blood fluids through said separator;

wherein said circuit for conducting blood, said separator and said open loop pneumatically driven pulsating pump are supported within a disposable housing.

2. The blood processor of claim 1 wherein said circuit for conducting blood is in fluid communication with a source of blood remote from said disposable housing.

3. The blood processor of claim 1 further comprising a circuit for introducing a wash fluid into said circuit for conducting blood which is supported in said disposable housing.

4. The blood processor of claim 3 further comprising an adjustable valve supported by said disposable housing to adjustably control the volume of wash fluid introduced into said circuit for conducting blood.

5. The blood processor of claim 4 wherein said valve further includes a pointer and a color chart having at least two color variations, whereby targeting said pointer at one of said at least two color variations on said color chart places said valve in a predetermined position which admits a predetermined volume of wash fluid into said circuit for conducting blood.

6. The blood processor of claim 5 wherein said color chart includes a translucent red-orange section, a translucent red section and an opaque purple section.

7. The blood processor of claim 6 wherein said value admits increasingly more wash fluid as said pointer is manipulated from said translucent red-orange section, to said translucent red section, to said opaque purple section of said color chart.

8. The blood processor of claim 5 wherein a portion of said circuit for conducting blood adjacent said adjustable valve is transparent.

9. The blood processor of claim 3 further comprising shutoff valves in said circuit for conducting blood and said circuit for introducing a wash fluid, whereby the flow of blood and wash fluid is selectively interruptible.

10. The blood processor of claim 3 wherein said circuit for conducting blood, said circuit for introducing a wash fluid, said open loop pneumatically driven pulsating pump and said separator are integrally formed as a unitary structure.

11. The blood processor of claim 3 further comprising one-way valves in said circuit for conducting blood and said circuit for introducing a wash fluid, to prevent back flow of blood and wash fluid when said circuits are in communication, respectively, with a source of blood and a source of wash fluid.

12. The blood processor of claim 3 further comprising a source of wash fluid remote from said disposable housing, wherein said circuit for introducing a wash fluid is in fluid communication with said source of wash fluid remote from said disposable housing.

13. The blood processor of claim 1 wherein said housing includes a port for directly connecting said open loop pneumatically driven pulsating pump to a pneumatic source.

14. The blood processor of claim 1 wherein said separator is a hollow fiber cell separator.

15. The blood processor of claim 1 wherein said open loop pneumatically driven pulsating pump includes an elastic membrane.

16. A method of separating blood into cellular blood components and blood fluids, comprising the steps of:
    providing a blood processor including a disposable housing supporting therein a circuit for conducting blood to be processed, an open loop pneumatically driven pulsating pump for pumping blood to be processed and a separator for separating blood into cellular blood components and blood fluids;
    connecting a source of blood whose components are to be separated to the circuit for conducting blood;
    continuously pumping blood with the open loop pneumatically driven pulsating pump along the circuit for conducting blood and into the separator without reversible flow at a frequency sufficient to agitate the blood therein so that the cellular components in the blood are inhibited from blocking passage of the blood fluids through the separator.

17. A method of separating blood into cellular blood components and blood fluids, comprising the steps of:
    providing a blood processor having a circuit for conducting blood to be processed, a circuit for introducing wash fluid into the circuit for conducting blood, and a separator for separating the blood into cellular blood components and blood fluids;
    connecting a source of blood whose components are to be separated to the circuit for conducting blood;
    observing the color of the blood flowing along the circuit for conducting blood and introducing a predetermined amount of wash fluid in response thereto to form an admixture;
    separating the admixture into blood cellular components and blood fluids in the separator.

18. The method of separating blood of claim 17 wherein the blood processor further includes a pump.

19. A blood processor for separating blood into cellular blood components and blood fluids, comprising:
    a circuit for conducting blood whose components are to be separated;
    a circuit for introducing a wash fluid into said circuit for conducting blood;
    a valve for regulating the introduction of wash fluid into said circuit for conducting blood and said valve including a reference having at least two different color variations which correspond to the color of blood which is to be separated, said valve being adjustable amongst said at least two different color variations to introduce a predetermined amount of wash fluid into said circuit for conducting blood; and
    a separator in communication with said circuit for conducting blood and said circuit for introducing a wash fluid for separating cellular blood components from blood fluids.

20. The blood processor of claim 19 wherein said valve includes a pointer and said reference includes a chart having at least two different color sections each of which are registrable by said pointer.

21. The blood processor of claim 20 wherein said chart includes a translucent red-orange section, a translucent red section and an opaque purple section.

22. The blood processor of claim 19 further including a pump for pumping blood and wash fluid through said separator.

23. The blood processor of claim 19 wherein said circuit for conducting blood, said circuit for introducing a wash fluid, said valve and said separator are supported in a disposable housing.

24. The blood processor of claim 19 wherein said separator includes a hollow fiber separator.

25. The blood processor of claim 19 further comprising a transparent chamber adjacent said valve for observing the color of blood flowing through said circuit for conducting blood.

26. A blood processor for separating blood into cellular blood components and blood fluids comprising:
    an elongated disposable housing;
    a blood inlet connectable to a source of blood to be separated;
    a wash fluid inlet connectable to a source of wash fluid for admixing with the blood to be separated;
    a valve in communication with said blood inlet and said wash fluid inlet and being selectively adjustable to vary the amount of wash fluid introduced into the blood to be separated, said valve including an outlet;
    an open loop, pneumatically driven elastic membrane pump having an inlet in communication with said valve outlet, a pump outlet and a port which is connectable to a source of pneumatic pressure, said pump adapted for pulsatile, non-reversible flow;
    a separator for separating blood into cellular components and blood fluids, said separator including an inlet fluidly connected to said pump outlet, said separator adapted to receive the blood fluid and wash fluid in an agitated state to inhibit the cellular components from blocking movement of the blood fluid and wash fluid through the separator;
    wherein said blood inlet, said wash fluid inlet, said valve, said open loop, pneumatically driven elastic membrane pump and said separator are supported in said elongated disposable housing.

* * * * *